United States Patent
Chandler et al.

(10) Patent No.: US 7,572,464 B2
(45) Date of Patent: Aug. 11, 2009

(54) SOLVENT EXTRACTION OF LIPIDS SUCH AS ESSENTIAL FATTY ACIDS

(75) Inventors: Anthony Michael Chandler, Cambridgeshire (GB); Peter Andrew Whitton, Leicester (GB); Andre Ka-chun Lau, Leicester (GB)

(73) Assignee: Bionovate Limited, Angle Drove, Ely (GB)

( * ) Notice: Subject to any disclaimer, the term of this patent is extended or adjusted under 35 U.S.C. 154(b) by 0 days.

(21) Appl. No.: 10/597,466

(22) PCT Filed: Jan. 28, 2005

(86) PCT No.: PCT/GB2005/000337

§ 371 (c)(1), (2), (4) Date: May 30, 2007

(87) PCT Pub. No.: WO2005/073354

PCT Pub. Date: Aug. 11, 2005

(65) Prior Publication Data

US 2007/0270600 A1 Nov. 22, 2007

(30) Foreign Application Priority Data

Jan. 30, 2004 (GB) .................. 0402146.5
May 19, 2004 (GB) .................. 0411164.7

(51) Int. Cl.
*A61K 35/60* (2006.01)
*C11B 1/10* (2006.01)

(52) U.S. Cl. ....................... 424/523; 424/522

(58) Field of Classification Search ................. 424/522, 424/523

See application file for complete search history.

(56) References Cited

U.S. PATENT DOCUMENTS

| 4,455,298 A | * | 6/1984 | McFarlane et al. .......... 424/547 |
| 4,801,453 A | * | 1/1989 | Kosuge et al. .............. 424/547 |
| 5,707,673 A | * | 1/1998 | Prevost et al. ............... 426/417 |
| 6,083,536 A |   | 7/2000 | Macrides et al. |
| 6,346,278 B1 |  | 2/2002 | Macrides |

(Continued)

FOREIGN PATENT DOCUMENTS

WO    WO 96/05164 A    2/1996

(Continued)

OTHER PUBLICATIONS

International Search Report for Application No. PCT/GB/2005/000337, dated Jan. 28, 2005.

(Continued)

*Primary Examiner*—Porfirio Nazario-Gonzalez
*Assistant Examiner*—Yate K Cutliff
(74) *Attorney, Agent, or Firm*—Conley Rose, P.C.

(57) ABSTRACT

Lipids (including fatty acids) are extracted from animal solids such as powdered, freeze dried or fresh meat of green lipped mussel (*Perna canaliculus*) by mixing said solids with a solvent such as acetone capable of dissolving lipids therefrom to form a solvent extract, removing solvent from said extract by nanofiltration to produce a concentrated lipid extract and recovered solvent, and removing further solvent from the concentrated extract by rotary evaporation to leave extracted lipids particularly rich in eicosatetraenoic acids (ETA's).

8 Claims, 1 Drawing Sheet

U.S. PATENT DOCUMENTS 6,596,303 B1 7/2003 Bui

FOREIGN PATENT DOCUMENTS

| WO | WO 97/09992 | * | 3/1997 |
| WO | WO 97/09992 A | | 3/1997 |
| WO | WO 96/18445 A | | 6/1998 |
| WO | WO 00/23546 | * | 4/2000 |
| WO | WO 00/23546 A | | 4/2000 |
| WO | WO 00/53198 | | 9/2000 |
| WO | WO 02/24211 | | 3/2002 |
| WO | WO 02/41978 A | | 5/2002 |
| WO | WO 02/092540 | | 11/2002 |
| WO | WO 03/011873 | | 2/2003 |
| WO | WO 03/043570 | | 5/2003 |

OTHER PUBLICATIONS

Geering, Richard; Engelke, Clare; and Chandler, Tony; "Polyunsaturated Fatty Acids—Are They Alternative Anti-inflammatories?"; European Companion Animal Health; Technology & Services Section; 4pp.; 2006.

* cited by examiner

SOLVENT EXTRACTION OF LIPIDS SUCH AS ESSENTIAL FATTY ACIDS

RELATED APPLICATIONS

This application claims benefit of PCT Application PCT/GB2005/000337 filed on Jan. 28, 2005, which claims benefit of United Kingdom Application No. 0402146.5 filed on Jan. 30, 2004, which claims the priority of United Kingdom Application No. 04111164.7 filed on May 19, 2004.

This invention relates to a new method for extracting lipids such as essential fatty acids from natural sources, particularly the New Zealand Green Lipped Mussel (*Perna canaliculus*)

Pharmacological Application of Lipid-Derived Omega-3 Series Poly-Unsaturated Fatty Acids from *Perna canaliculus*

The anti-arthritic properties of the New Zealand Green Lipped Mussel (*Perna canaliculus*) have been reviewed for nearly 30 years. More recently the range of omega-3 series PUFAs naturally present in *Perna canaliculus* have been evaluated for their anti-inflammatory and anti-asthmatic properties. These marine-derived lipids have been shown to possess potent anti-inflammatory properties by inhibiting the action of the two enzymes, cyclo-oxygenase and lipoxygenase.

The most common product presentation is a solid tablet containing powdered material derived from the tissues of the Green Lipped Mussel. The majority of the tablet is protein and the PUFA content is consequently low. Thus, with a typical intake of one or two tablets per day the effective daily dose falls below that considered to be effective in mammals. Extracting the PUFAs as an oil and presenting the product as a capsule, or as a tablet containing oil absorbed to a carrier, is a more efficient way of ensuring an adequate dose.

US 63462278 describes a method of anti-inflammatory treatment of a human or animal patient comprising administration of a lipid extract of *Perna canaliculus*. U.S. Pat. No. 6,596,303 describes the alleviation of arthritic symptoms in animals by administering powdered *Perna canaliculus* in the feed. WO03043570A2 describes formulations and methods of treatment of inflammatory conditions comprising an omega-3 fatty acid, such as DHA, or a flavonoid with a non-alpha tocopherol. WO03011873A2 describes a phospholipid extract from a marine biomass comprising a variety of phospholipids, fatty acid, metals and a novel flavonoid. WO02092450A1 describes the production and use of polar-rich fractions containing EPA, DHA, AA, ETA and DPA from marine organisms and others and their use in humans food, animal feed, pharmaceutical and cosmetic applications.

The lipids extracted from the Green Lipped Mussel have been shown to contain particular types of fatty acids not found in the same proportion in other organisms. These omega-3 series PUFAs have only recently been characterized due to advances in manufacturing. It is essential that cold processing and suitable drying methods are used to preserve the delicate structures of these particular fatty acids. The omega-3 series content is known to include the PUFAs: EPA, DHA and the ETAs (eicosatetraenoic acids).

The ETAs have a similar structure to the omega-6 series arachidonic acid but have been shown to be profoundly more potent than EPA, DHA or a-LNA in inhibiting the production of proinflammatory prostaglandins, thromboxanes and leukotrienes. ETAs have been shown to be as potent as ibuprofen and aspirin in independent studies and 200 times more potent than EPA in the rat paw oedema test (Whitehouse M W et al, Inflammopharmacology 1997; 5:237-246).

Pharmacologically, lipid derived from *Perna canaliculus* has been shown to significantly inhibit cyclo-oxygenase 2 and lipoxygenase pathways following in vitro studies that determined the $IC_{50}$ for each:

Cyclo-oxygenase 2 $IC_{50}$=1.2 µg/ml

Lipoxygenase $IC_{50}$=20 to 50 ug/ml

Therefore, the lipids occurring naturally in *Perna canaliculus* exhibit significant anti-inflammatory activity in vitro and in vivo Lipid Extraction Methods The extraction of essential fatty acids such as the polyunsaturated fatty acids ETA and EPA from raw material sources has been carried out routinely by simple solvent extraction, followed by evaporation and recovery of the solvent. Alternatively, supercritical carbon dioxide has been used as a solvent eg. U.S. Pat. No. 6,083,536. The disadvantage of the former method is that heat must be used to evaporate the considerable quantities of solvent used and this leads to degradation of the active PUFA content. The advantage of the latter method is that there is no requirement to remove solvent at the end of the extraction process, but the principal disadvantage of supercritical carbon dioxide as a solvent is that it is less suitable for extracting fatty acids. The final product oil contains significantly lower levels of PUFAs than the standard organic solvent extraction techniques.

Nanofiltration membranes have been used in extraction processes in the pharmaceutical and fine chemicals industry where product retention is important eg. WO0241978A1. The membranes are used to remove nonvolatile species such as solvents and recover residual reagents at the end of a reaction. Nanofiltration membranes are known to reduce yield loss after repeated extractions and are usually available in four cut-off weights: 200, 220, 280 and 400 Da. The use of nanofiltration membranes has not been reported in the extraction of essential fatty acids from natural product sources.

BRIEF DESCRIPTION OF THE DRAWINGS

The accompany drawing illustrates the invention.

DESCRIPTION OF THE INVENTION

Figure 1:
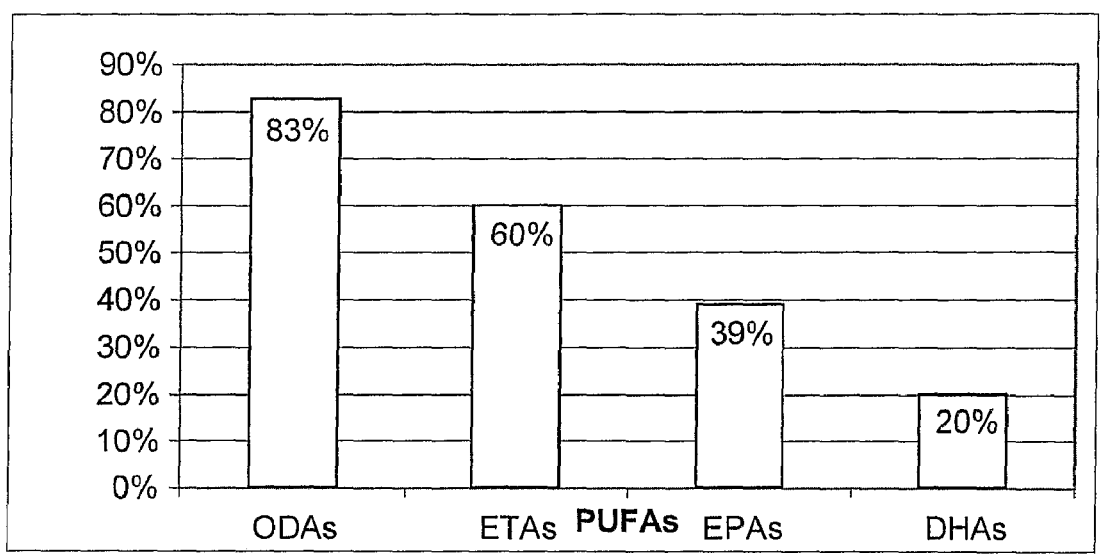
FIG. 1 is a summarization of the percentage improvement in yield from the membrane process.

Accordingly, the invention now provides a process for the extraction of lipids including lipid fatty acids and essential fatty acids from animal solids comprising mixing said solids with a solvent capable of dissolving lipids therefrom to form a solvent extract, removing solvent from said extract by nanofiltration to produce a concentrated lipid extract and recovered solvent, and removing further solvent from the concentrated extract by evaporation to leave extracted lipids, suitably by evaporation, e.g. rotary evaporation.

The process may be applied where said animal solids are dried animal flesh, for instance dried animal flesh such as powdered, freeze dried, or spray dried meat of green lipped mussel (*Perna canaliculus*). It is also feasible to extract fatty acids directly from fresh tissue using a suitable organic solvent in which the compounds have a high solubility and which may or may not be miscible with water.

Preferably, the solvent is one that can be removed from the resulting extract by evaporation at or below room temperature, i.e. has sufficient volatility, such as acetone hexane or ethyl acetate. Alternatively the solvent can be removed in a phase separation procedure if it is immiscible with water, for example, the concentrated solvent extract is mixed with water. In this case the lipids will partition into the aqueous phase at a suitable pH and the aqueous phase can be separated and can then be dried or freeze dried. The aqueous phase may be made sufficiently alkaline that the free fatty acids partition into it from the organic solvent.

The nanofiltration is preferably conducted as crossflow nanofiltration which may be performed using a nanofiltration material having a cut off for normal alkanes dissolved in toluene giving 90% rejection at 300 Da or below, e.g one where said cut off is above 100 Da. Suitable materials include the STARMEM™ nanofiltration membranes or other polyimide based membranes. These may be employed in spiral wound modules, typically using pressure in the region of 60 bar.

The evaporation is preferably conducted by rotary evaporation, which is preferably done at a temperature of at or below ambient, e.g. at a temperature of at or below 20° C.

A new method of extracting lipids, especially essential fatty acids, from animal-derived materials has been developed. In preferred aspects the method is based on the use of an organic solvent to dissolve fatty acids from a dried raw material source, preferably a powder of Green Lipped Mussel tissue. The preferred solvent is pharmaceutical-grade acetone. The powder material is preferably stirred in the solvent and the solvent containing extracted oil is then pumped through a defined pore size nanofiltration membrane that retains the essential fatty acids whilst allowing solvent molecules to pass through. One of the main advantages of the invention is that the extraction and filtration process can be operated at, or below, ambient temperature to ensure the best yield of active PUFAs. There is no need to evaporate large volumes of solvent from the extracted oil using heat, as the solvent is largely removed in the membrane process in a continuous flow procedure. So the whole extraction process is very energy-efficient.

The organic solvent will extract a wide range of compounds, such as phospholipids and triglycerides as well as the free fatty acids. A further advantage of the extraction process is that the smaller molecular weight lipids and fatty acids pass through the filter and therefore do not form a significant component of the final concentrated oil. Thus the product is enriched in the beneficial long chain unsaturated fatty acids and depleted in the short chain saturated fatty acids compared to oils prepared by other extraction methods.

Analyses have shown that the PUFA content of the extracted oil from the nanofiltration process is considerably higher than that obtained with the supercritical carbon dioxide process (see Table 1). Thus the nanofiltration membrane extraction process will deliver a product from Green Lipped Mussel powder that is much more biologically active.

A further aspect of the invention is the use of two nanofiltration membranes with different molecular weight cut-offs. This allows the selection of a narrower molecular weight fraction of the essential fatty acids. For example using a 400 Da cut-off filter first in a filter cartridge followed by a 200 Da filter will yield an oil product recovered from between these two membranes that is selectively enriched in compounds with molecular weight between 200 and 400 Da.

The accompanying drawing shows results obtained in Example 3 for the improvement in PUFA content using a membrane extraction process compared to the starting mussel powder.

EXAMPLES

Example 1

100 g of dried Green Lipped Mussel powder was suspended in 200 ml of pharmaceutical grade acetone and stirred for one hour. The suspension was filtered through a coarse filter to remove the undissolved powder and then the filtrate containing essential fatty acids was pumped continuously through a controlled pore nanofiltration membrane (Starmem 400, Grace Davison, US). The oil retained by the nanofiltration membrane was collected and returned to the mussel powder extraction vessel. After 60 minutes of pumping the oil retained by the nanofiltration membrane was placed in a rotary evaporator and residual solvent was removed under vacuum at ambient temperature (22° C.).

The analysis of the extracted oil was:

PUFA content 15.7%

As a comparison the reported specification of a commercially available supercritical carbon dioxide extract is:

PUFA content 5.8%

Example 2

Extraction of PUFAs from Green Lipped Mussel Powder

The experimental procedure was:
1) Weigh out known mass (1 kg) of mussel powder into light-proof container
2) Add 10 L of acetone to container
3) Insert overhead stirrer and mix for 60 min at ambient temperature (22° C.)
4) After 60 min, turn off stirrer and allow solids to settle for 60 min
5) Decant PUFA solution from container, whilst retaining solids
6) Transfer PUFA solution to filtration feed vessel of crossflow filtration system
7) Filter PUFA solution at 30 bar, 20° C. using STARMEM 122 (Grace Davison Inc.), 220 Da nominal cut off.
8) Continue until PUFA solution volume has been reduced by 80%
9) Transfer retentate (concentrated PUFA solution) to rotovap vessel
10) Carry out evaporation in the rotovap at ambient temperature (22° C.) (no heat addition to the system so the vessel chills significantly as the acetone initially evaporates) and maximum vacuum, using a water condenser and liquid nitrogen vacuum trap.
11) Once evaporation end-point reached (essentially no boiling and frothing of the PUFA oil), release the vacuum and transfer the oil to a lightproof container for storage.

An analysis of the extracted oil is shown in Table 1.

TABLE 1

Analytical profile of fatty acids in whole *Perna canaliculus* dried powder and lipid extracts
The results shown below confirm that the acetone-extracted lipids are rich in omega-3 series PUFAs including octadecatetraenoic acids (C18:4n2) and eicosatetraenoic acids (C20:4n3). Supercritical $CO_2$ produces a poor lipid extract in terms of omega-3 series yield

| Green Lipped Mussel Oil Samples | Published $CO_2$ extraction | Acetone extraction/ Membrane filtration | Whole Mussel Powder |
|---|---|---|---|
| C14.0 Myristic acid | 1.5 | 5.6 | 5.7 |
| C14.1 Myristoleic acid | 0.1 | 0.2 | 0.1 |
| CI5.0 Pentadecanoic acid | 0.2 | 0.8 | 1.1 |
| C16.0 Palmitic acid | 14.3 | 16.3 | 17.2 |
| C16.1 Palmitoleic acid | 3.2 | 10.2 | 10 |
| C17.0 Heptadecanoic acid | 0.3 | 1.7 | 2 |
| C17.I Heptadecenoic acid | 0.1 | 0.9 | 4.5 |
| C18.0 Stearic acid | 3.3 | 2.9 | 4.4 |
| C18.1 Oleic acid | 4.8 | 6 | 5.3 |
| C18.2 Linoleic acid | 9 | 2.7 | 1.9 |
| C18.3 Linolenic acid (omega 3) | 1.2 | 2.8 | 1.8 |
| CI 8.3 Linolenic acid (omega 6) | 0.6 | 0.6 | 0.5 |
| C18.4 Octadecatetraenoic acid |  | 4.5 | 2.7 |
| C20.0 Arachidic acid | 0 | 0.1 | 0.5 |
| C20.1 Gadoleic acid |  | 4.1 | 5.8 |
| C20.2 Eicosadienoic acid |  | 0.7 | 0.6 |
| C20.3 Eicosatrienoic acid (omega 3) | 0.1 | 0.2 | 0.2 |
| C20.3 Eicosatrienoic acid (omega 6) |  | 0.4 | 0.4 |
| C20.4 Eicosatetraenoic acid (omega 3) | 0.3 | 0.5 | 0.3 |
| C20.4 Arachidonic acid (omega 6) |  | 1.3 | 1.8 |
| C20.5 Eicosapentaenoic acid | 5 | 22.5 | 19.5 |
| C22.0 Behenic acid | 0 | 0.1 |  |
| C22.1 Cetoleic acid | 0 | 0.1 | 1.5 |
| C22.4 Docosatetraenoic acid | 0.2 | 2.1 | 1.4 |
| C22.5 Clupanodonic acid | 0.3 | 1 | 1.1 |
| C22.6 Docosahexaenoic acid | 3.9 | 11.8 | 9.6 |
| Quantity of ETAs mg per 100 g | 141 | 395 | 192 |
| Quantity of EPAs mg per 100 g | 2,350 | 17,775 | 12,480 |
| Quantity of DHAs mg per 100 g | 1,833 | 9,322 | 6,144 |

For each acid listed above, the figures in the next three columns represent the percentage of total extracted material made up by that acid, not all components of the material being reported. Yields of the fatty acids may be determined by the inclusion with the mussel powder starting material of a known amount of lipid standard and quantitating the recovery of the standard. The process of the invention has produced a 45% yield.

Example 3

Reproducibility of Extraction of PUFAs from Green Lipped Mussel Powder

Table 2 shows experimental data from three different membrane extraction runs carried out according to Example 2. The results show that the method is reproducible in the yield of PUFAs obtained in the oil. The % improvement in yield from the membrane process is summarised in FIG. 1.

TABLE 2

Comparison of three PUFA extractions from mussel powder using the nanofiltration membrane process

| Fatty acid composition (as % of eluted methyl esters) | Mussel Powder | Extraction 1 | Extraction 2 | Extraction 3 |
|---|---|---|---|---|
| C14.0 Myristic acid | 4.5 | 5.9 | 5.7 | 5.5 |
| C14.1 Myristoleic acid | 0.1 | 0.3 | 0.1 | 0.1 |
| CI5.0 Pentadecanoic acid | 1.3 | 1.1 | 1.3 | 1.1 |
| C16.0 Palmitic acid | 18.1 | 19 | 18.7 | 18.2 |
| C16.1 Palmitoleic acid | 8.8 | 11 | 10.8 | 10.9 |
| C17.0 Heptadecanoic acid | 1.9 | 1.8 | 1.8 | 1.9 |
| C17.I Heptadecenoic acid | 4.1 | 1 | 1 | 1 |
| C18.0 Stearic acid | 4.4 | 3.2 | 3.2 | 3.1 |
| C18.1 Oleic acid | 5.4 | 6 | 6 | 5.9 |
| C18.2 Linoleic acid | 2.3 | 2.5 | 2.5 | 2.5 |
| C18.3 Linolenic acid (omega 3) | 2.1 | 2.6 | 2.6 | 2.6 |
| CI 8.3 Linolenic acid (omega 6) | 0.4 | 0.5 | 0.5 | 0.5 |
| C18.4 Octadecatetraenoic acid | 2.5% | 3.5% | 3.8% | 3.9% |
| C20.0 Arachidic acid | 4 | 0.5 | 0.2 | <0.1 |
| C20.1 Gadoleic acid | 3.9 | 5.2 | 5.1 | 5.5 |
| C20.2 Eicosadienoic acid | 1.2 | 1.2 | 1.2 | 1 |
| C20.3 Eicosatrienoic acid (omega 3) | 0.2 | 0.2 | 0.2 | 0.3 |
| C20.3 Eicosatrienoic acid (omega 6) | 1 | 0.3 | 0.3 | 0.8 |
| C20.4 Eicosatetraenoic acid (omega 3)(AA) | 0.3% | 0.4% | 0.4% | 0.4% |
| C20.4 Arachidonic acid (omega 6) | 1.5 | 1.2 | 1.2 | 1.3 |
| C20.5 Eicosapentaenoic acid | 15.2% | 17.2% | 17.6% | 18.1% |
| C22.0 Behenic acid | <0.1 | <0.1 | <0.1 | <0.1 |
| C22.1 Cetoleic acid | 1.5 | <0.1 | <0.1 | <0.1 |
| C22.4 Docosatetraenoic acid | 1 | 1.8 | 1.8 | 1.5 |
| C22.5 Clupanodonic acid | 1 | 0.8 | 0.8 | 0.8 |
| C22.6 Docosahexaenoic acid | 8.7% | 8.5% | 8.7% | 8.7% |

Example 4

Suppression of Nitric Oxide (NO) Production in LPS Stimulated Murine Macrophages by GLM Lipid Extract A preparation of murine macrophages or RAW264 cells was challenged with lipopolysaccharide (LPS). The cells are stimulated to secrete nitric oxide (NO) and this was measured with a commercially available kit. Secretion of this cell signalling compound is an indication of the inflammatory response of the cells to the challenge agent. The addition of PUFA oil extract made according to Example 2 inhibited the secretion of NO by the cells.

In this example foetal calf serum (FBS), Lipopolysaccharide (*Escherichia coli,* 0111:B4) (LPS), Trypan Blue, and L-glutamine supplemented with 100 U/ml penicillin and 100 μg/ml streptomycin were obtained from Sigma Aldrich (Gillingham, Dorset, UK). Phosphate buffered saline (PBS) (Ca and Mg free), L-glutamine, and RPMI 1640 (phenol free) was purchased from Invitrogen (Paisley, UK). Cell scrapers were obtained from Greiner Bio-One (Gloucester, UK) and pipettes and plastic ware were obtained from VWR (Poole, UK). Griess Reagent Systems were supplied by Promega (UK). RAW 264.7 cells were kindly donated by Dr Nicola Dalbeth at Imperial College London.

The RAW264.7 cells (Fang et al., 2004; Patel et al., 1999) were cultured in RPMI 1640 medium, supplemented with 10% FBS and 1% L-glutamine (with penicillin/streptomycin), at 37° C. in a humidified incubator with 5% $CO_2$. Cells were subcultured at 70-80% confluence. Cells were plated in six well trays and cells grown to 90% confluency. Media was aspirated and LPS added at concentrations of 0.01 μg/ml, 0.1 μg/ml, 1 μg/ml, 10 μg/ml and 100 μg/ml. The cells were incubated for a further 24 hours before results were read. This experiment was performed and assayed in triplicate.

For NO experiments, cells were plated at $6\times10^2$ per ml of culture media in 24 well plates and incubated for approximately 48 hours or until they reached 90% confluency. GLM lipid extract was mixed 1:1 in 99% ethanol and diluted in media accordingly. Media was aspirated from the cells and replaced with media containing 1 μg/ml LPS and varying GLM lipid extract concentrations (0-5 μg/ml). Ethanol was taken to a 1% final volume in the media before it was administered to cells. Cells were incubated for a further 24 hrs before media was aspirated and frozen (−80° C.). This experiment was repeated six times and assayed in duplicate. A Griess reagent kit was used to test for nitrite production (a stable, non-volatile breakdown product of NO). Cell samples were defrosted in a water bath at 37° C. and spun at 3000 rpm for 10 minutes to remove particulates. Samples at a concentration of 5 μg/ml GLM lipid extract were filtered to remove excess oil. Previous results indicate that this has no effect on NO concentration. After preparation of a standard curve (0-100 μM), 50 μl of each sample was dispensed, in duplicate, into a 96 well plate. Sulphanilamide solution, 50 μl, was added to each well. Plates were incubated, in the dark, for 7.5 minutes and 50 μl N-1 napthylethylenediamine dihydrochloride solution added, followed by a second incubation. Plates were then read at 492 nm. Absorbance between duplicates was not to have a critical value below 0.5, or the assay was repeated

TABLE 3

NO production (triplicate average) with varying LPS concentration repeated in triplicate.

| LPS Concentration | 1 | 2 | 3 | Average |
|---|---|---|---|---|
| 0 ug/ml LPS | 0.392 | 0.892 | 0.738 | 0.674 |
| 0.01 ug/ml LPS | 3.070 | 3.122 | 3.044 | 3.079 |
| 0.1 ug/ml LPS | 28.822 | 29.917 | 28.863 | 29.201 |
| 1.0 ug/ml LPS | 39.402 | 39.919 | 39.583 | 39.635 |
| 10 ug/ml LPS | 39.097 | 39.291 | 40.517 | 39.635 |
| 100 ug/ml LPS | 31.749 | 32.238 | 31.314 | 31.767 |

TABLE 4

GLM lipid extract suppression of NO production by RAW264.7 under LPS challenge (duplicate experiements, average of six samples)

| Media | 1 <min | 2 <min | 3 <min | 4 <min | 5 <min | 6 <min | Average <min |
|---|---|---|---|---|---|---|---|
| Control | 42.15 | 42.10 | 41.83 | 44.95 | 42.88 | 40.79 | 42.45 |
| 5 ug/ml (GLM) | 7.11 | 6.32 | 7.78 | 5.52 | 4.27 | 6.14 | 6.19 |
| 1 ug/ml | 13.38 | 10.64 | 14.60 | 11.95 | 13.12 | 11.63 | 12.55 |
| 0.5 ug/ml | 15.36 | 18.64 | 15.78 | 14.58 | 17.84 | 15.34 | 16.26 |

TABLE 4-continued

GLM lipid extract suppression of NO production by RAW264.7 under LPS challenge (duplicate experiements, average of six samples)

| Media | 1 <min | 2 <min | 3 <min | 4 <min | 5 <min | 6 <min | Average <min |
|---|---|---|---|---|---|---|---|
| 0.1 ug/ml | 33.93 | 31.76 | 32.65 | 33.74 | 33.63 | 33.93 | 33.27 |
| 0.05 ug/ml | 36.63 | 37.11 | 37.32 | 38.04 | 37.25 | 37.69 | 37.34 |
| 0.01 ug/ml | 40.24 | 41.65 | 42.33 | 41.00 | 41.01 | 41.00 | 41.20 |

REFERENCES

*Regulation of nitric oxide and prostaglandin $E_2$ production by CSAIDS™ (SB203580) in murine macrophages and bovine chondrocytes stimulated with LPS*) R. Patel, M. G. Attur, M. N. Dave, S. Kumar, J. C. Lee, S. B. Abramson and A. R. Amin, Inflamm. Res. 48 (1999) 337-343.

*Lipopolysaccharide-Induced Macrophage Inflammatory Response id regulated by SHIP* H. Fang, R. A. Pengal, X. Cao, L. P. Ganesan, M. D. Wewers, C. B. Marsh, S. Tridandapani. J. Immunol. 173 (2004)

The invention claimed is:

1. A process for the extraction of lipids including fatty acids from *Perna canaliculus* solids comprising mixing said solids with a solvent capable of dissolving lipids therefrom to form a solvent extract, removing solvent from said extract by nanofiltration to produce a concentrated lipid extract and recovered solvent, and removing further solvent from the concentrated extract to leave extracted lipids, wherein the solvent is selected from the group consisting of acetone, hexane and ethyl acetate.

2. A process as claimed in claim 1, wherein said *Perna canaliculus* solids are powdered, freeze dried or fresh meat of green lipped mussel.

3. A process as claimed in claim 1, wherein the nanofiltration is conducted using a nanofiltration material having a cut off for normal alkanes dissolved in toluene giving 90% rejection at 300 Da or below.

4. A process as claimed in claim 3, wherein said cut off is above 100 Da.

5. A process as claimed in claim 1, wherein said removing of further solvent is conducted by evaporation.

6. A process as claimed in claim 5, wherein said evaporation is conducted by rotary evaporation.

7. A process as claimed in claim 6, wherein the rotary evaporation is conducted at a temperature of at or below ambient temperature.

8. A process as claimed in claim 7, wherein the rotary evaporation is conducted at a temperature of at or below 20° C.

* * * * *